United States Patent
Ruan

(10) Patent No.: US 9,498,579 B2
(45) Date of Patent: Nov. 22, 2016

(54) SAFETY NEEDLE ASSEMBLY

(75) Inventor: Tieming Ruan, Stony Brook, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 535 days.

(21) Appl. No.: 13/699,515

(22) PCT Filed: May 26, 2010

(86) PCT No.: PCT/US2010/036200
§ 371 (c)(1),
(2), (4) Date: Dec. 14, 2012

(87) PCT Pub. No.: WO2011/149455
PCT Pub. Date: Dec. 1, 2011

(65) Prior Publication Data
US 2013/0110051 A1    May 2, 2013

(51) Int. Cl.
*A61M 5/32*    (2006.01)

(52) U.S. Cl.
CPC ......... *A61M 5/3232* (2013.01); *A61M 5/3257* (2013.01); *A61M 5/3271* (2013.01); *A61M 2005/3247* (2013.01)

(58) Field of Classification Search
CPC .. A61M 5/32; A61M 5/3251; A61M 5/3232; A61M 5/3243; A61M 5/3271; A61M 2005/3247; A61M 5/3247
USPC .......................................................... 604/198
See application file for complete search history.

(56) References Cited

U.S. PATENT DOCUMENTS

| | | | |
|---|---|---|---|
| 2002/0004648 A1* | 1/2002 | Larsen | A61M 5/326 604/195 |
| 2003/0120209 A1* | 6/2003 | Jensen et al. | 604/110 |
| 2004/0236284 A1 | 11/2004 | Hoste et al. | |
| 2005/0277895 A1 | 12/2005 | Giambattista et al. | |
| 2009/0005742 A1 | 1/2009 | Liversidge | |
| 2010/0016803 A1 | 1/2010 | Liversidge | |
| 2012/0179110 A1 | 7/2012 | Gratwohl et al. | |

FOREIGN PATENT DOCUMENTS

| | | | |
|---|---|---|---|
| EP | 1949929 A1 | 7/2008 | |
| WO | 0191837 A1 | 12/2001 | |

(Continued)

*Primary Examiner* — Theodore Stigell
*Assistant Examiner* — Tiffany Legette
(74) *Attorney, Agent, or Firm* — Dickinson Wright PLLC

(57) ABSTRACT

A safety needle assembly is provided herein having a hub; a needle fixed to the hub; a shield; a tab; a spring disposed between the shield and the hub configured to bias the shield distally; and, a clip disposed between the hub and the shield, the clip having a notch formed thereon shaped to permit passage therethrough of the tab. The clip and the tab releasably retain the shield in a first locked state against the biasing force of the spring thereby limiting distal movement of the shield relative to the hub; yet, in the first locked state, the shield is movable proximally relative to the hub. In the first locked state, the notch is spaced from the tab. The clip and the tab are relatively displaceable so as to align the notch with the tab and release the shield from the first locked state thereby allowing the shield to move distally, relative to the hub, to a second shielded state. In the second shielded state, the distal end of the needle is covered by the shield. Advantageously, with the subject invention, a passive safety needle assembly may be provided which requires few parts and is reliable.

8 Claims, 17 Drawing Sheets

(56) References Cited

FOREIGN PATENT DOCUMENTS

| WO | 2009102612 A1 | 8/2009 |
| WO | 2009114762 A1 | 9/2009 |
| WO | 2009114777 A1 | 9/2009 |
| WO | 2010019936 A1 | 2/2010 |

* cited by examiner

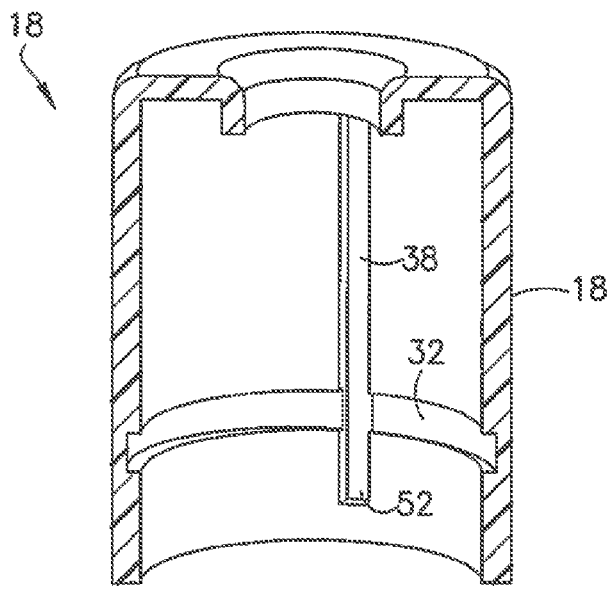
FIG.14
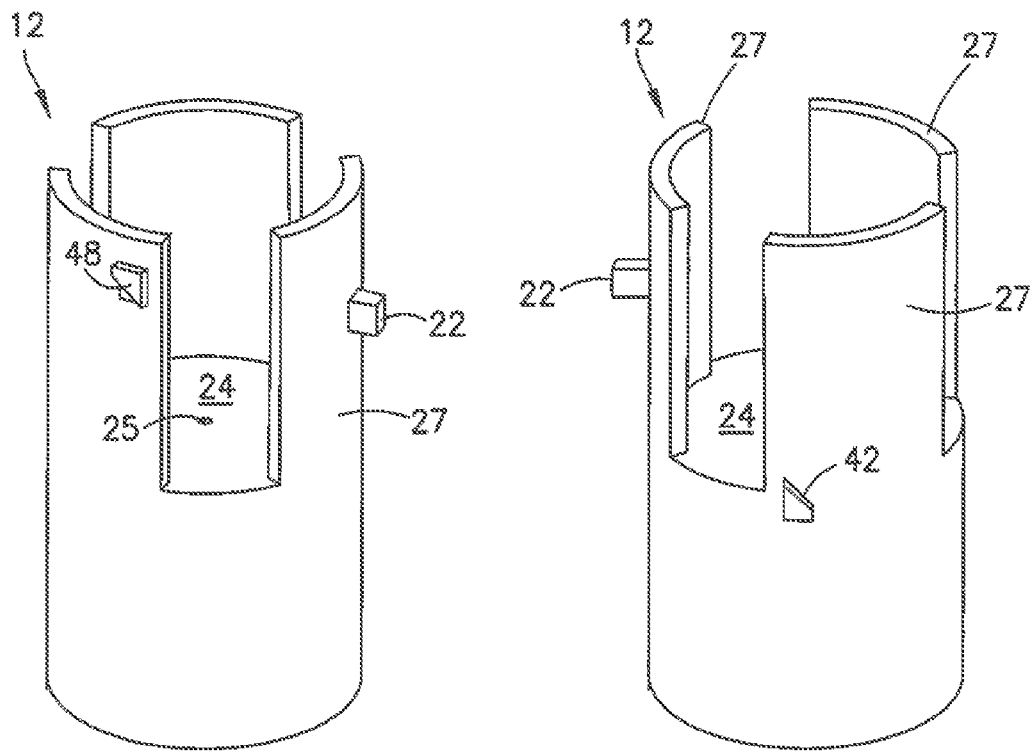
FIG.15
FIG.16

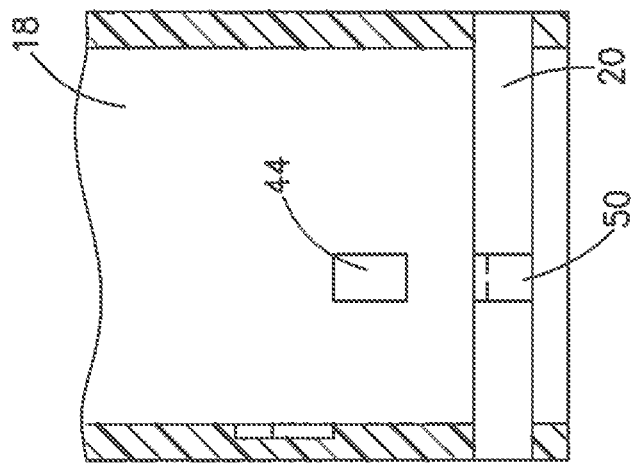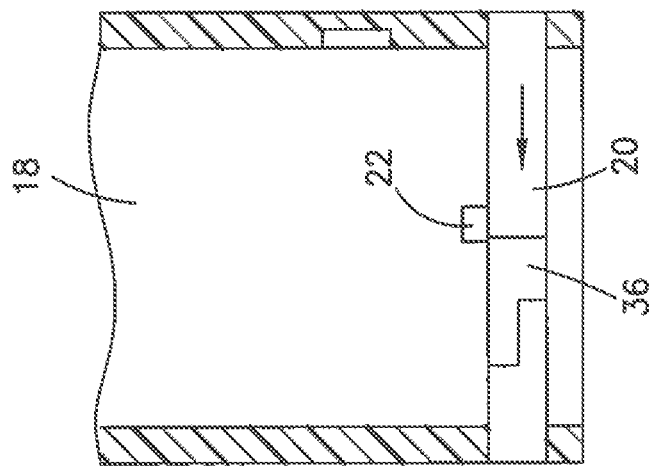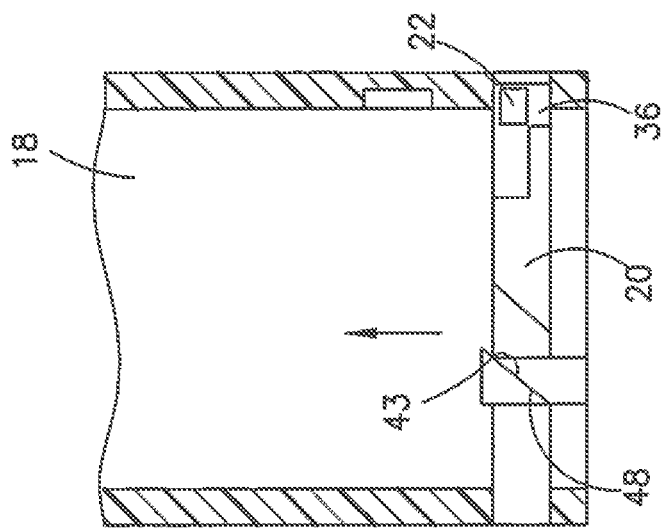

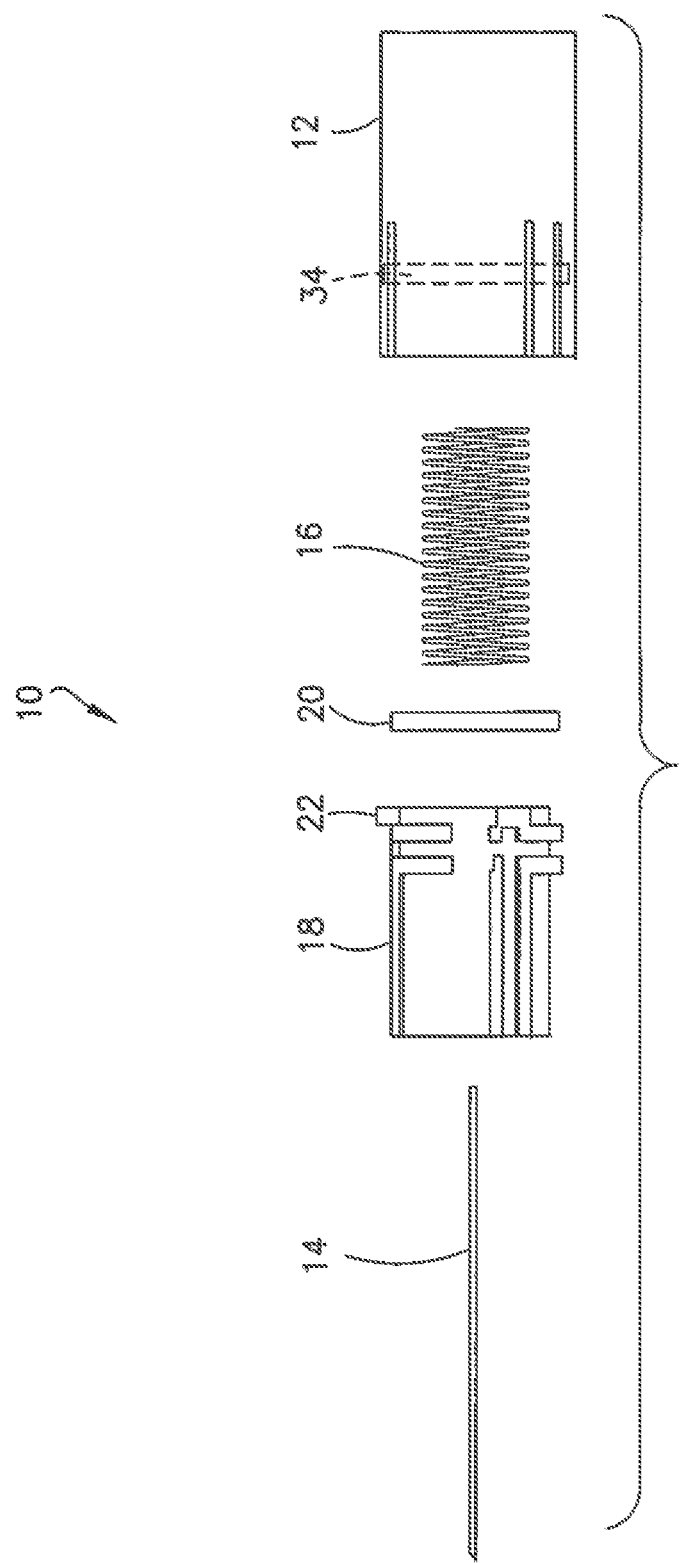

SAFETY NEEDLE ASSEMBLY

FIELD OF THE INVENTION

This invention relates to needle assemblies, more particularly, to safety needle assemblies.

BACKGROUND OF THE INVENTION

Pen injectors are known in the prior art and typically include a pen needle for insertion into a patient to allow proper drug administration. Such pens may be disposable, containing a single dose of a drug, or reusable, containing a single dose or more of a drug. The pen needle includes a double-ended needle with a distal end formed for insertion into a patient and a proximal end formed for insertion into a drug vial or cartridge located inside a pen injector body. The pen needle should be single-use and replaced with each administered dose.

Safety pen needle assemblies have been developed in the prior art which shield a pen needle after use. Typically, with this arrangement, after an injection, a lock mechanism locks a shield over the patient end of a safety pen needle and prevents reusage. The lock mechanisms of current safety pen needle assemblies implicate various considerations, including cost and manufacturing. Reliability is highly desired.

SUMMARY OF THE INVENTION

A safety needle assembly is provided herein having a hub; a needle fixed to the hub; a shield; a tab; a spring disposed between the shield and the hub configured to bias the shield distally; and, a clip disposed between the hub and the shield, the clip having a notch formed thereon shaped to permit passage therethrough of the tab. The clip and the tab releasably retain the shield in a first locked state against the biasing force of the spring thereby limiting distal movement of the shield relative to the hub; yet, in the first locked state, the shield is movable proximally relative to the hub. In the first locked state, the notch is spaced from the tab. The clip and the tab are relatively displaceable so as to align the notch with the tab and release the shield from the first locked state thereby allowing the shield to move distally, relative to the hub, to a second shielded state. In the second shielded state, the distal end of the needle is covered by the shield. Advantageously, with the subject invention, a passive safety needle assembly may be provided which requires few parts and is reliable.

As used herein, the term "distal", and derivatives thereof, refers to a direction towards a patient during use. The term "proximal", and derivatives thereof, refers to a direction away from a patient during use.

These and other features of the invention will be better understood through a study of the following detailed description and accompanying drawings.

BRIEF DESCRIPTION OF THE DRAWINGS

FIGS. 2-16 depict an embodiment of the subject invention where the clip is mounted to the shield; and, FIGS. 17-27 depict an embodiment of the subject invention where the clip is mounted to the hub.

DETAILED DESCRIPTION OF THE INVENTION

Figure 1:
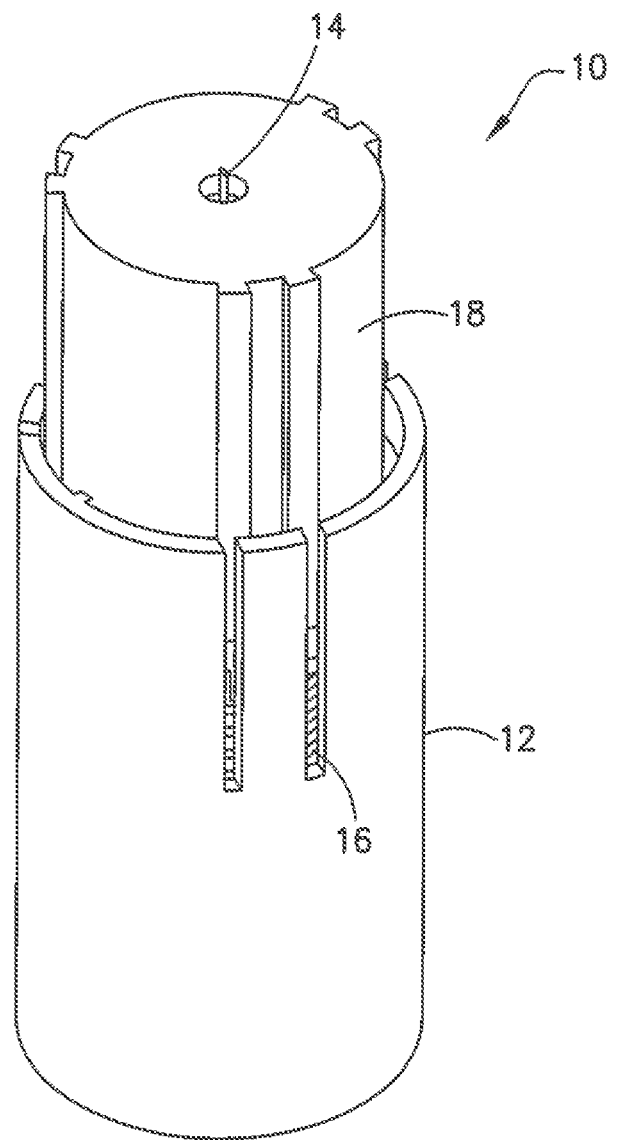
FIG. 1 depicts a perspective view of a safety needle assembly formed in accordance with the present invention.

With reference to the Figures, a safety needle assembly 10 is depicted. The assembly 10 is useable with various injectors but is particularly well-suited for use as a safety pen needle assembly with pen injectors. The assembly 10 generally includes a hub 12 fixed to a needle 14, a spring 16, a shield 18, a clip 20, and a tab 22, as shown in FIGS. 1-5.

Figure 6:
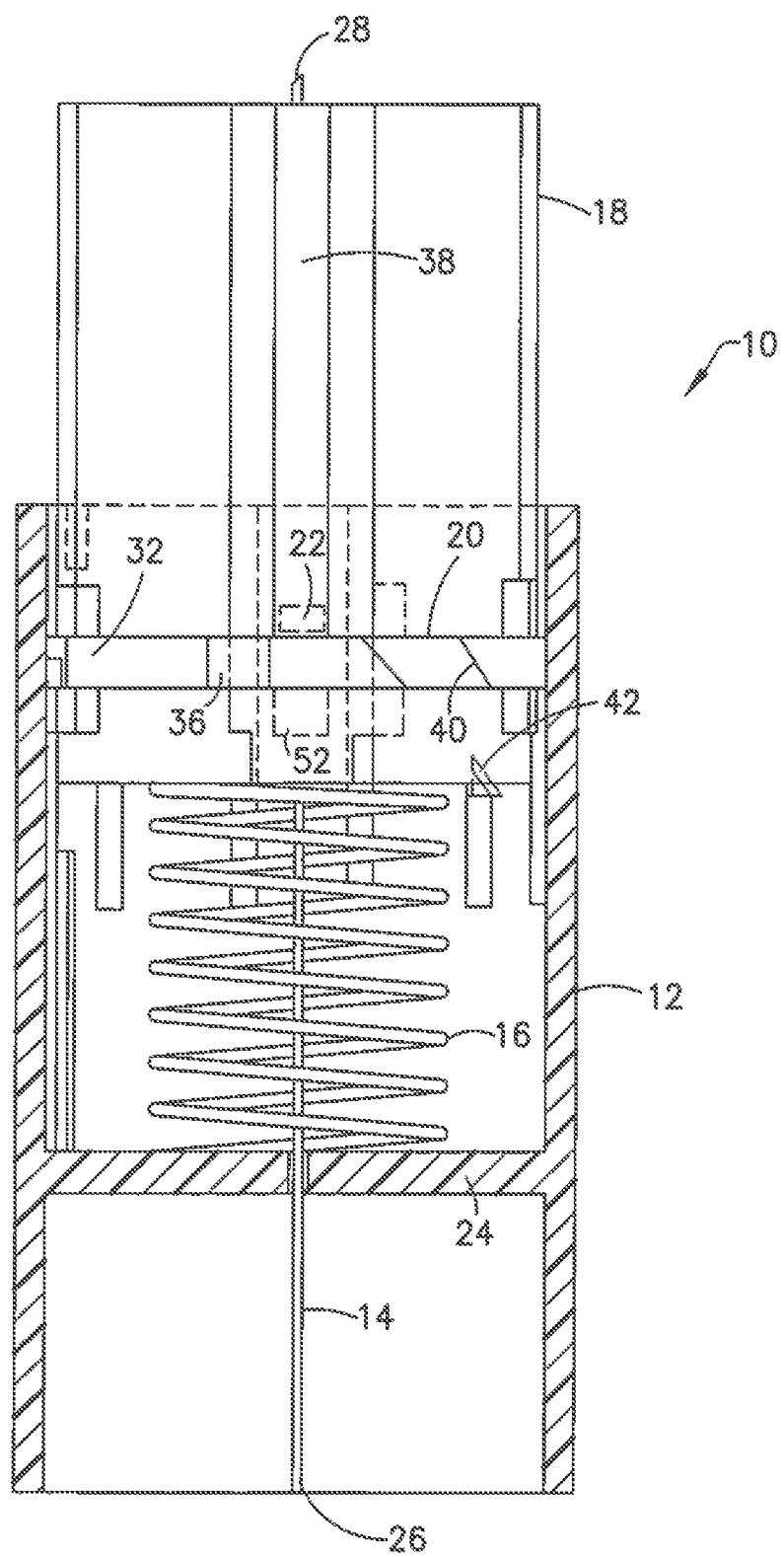

The hub 12 is generally tubular and includes a cross-piece 24 which extends at least partially across the interior thereof. The needle 14 passes through and is fixed to the cross-piece 24 in any known manner (e.g., being fixed by adhesive in opening 25 formed in the cross-piece 24 (FIG. 4)). The needle 14 includes a proximal end 26, located proximally of the cross-piece 24, and a distal end 28, located distally of the cross-piece 24 (FIG. 6). The distal end 28 is formed for insertion into a patient.

The shield 18 is disposed distally of the cross-piece 24. The shield 18 preferably is made of a polymeric material (e.g., thermoplastic) and preferably telescoped inside the hub 12. In this manner, the hub 12 is exposed for handling by a user, particularly in mounting the assembly 10 onto an injector body. Alternatively, the hub 12 may sit inside the shield 18. However, this arrangement may be less desired in that the hub 12 may be obscured for mounting. It is desired to avoid contact with the shield 18 during mounting or dismounting of the assembly 10.

The spring 16 is a biasing mechanism, preferably a compression spring, that sits between the shield 18 and the hub 12, preferably between the shield 18 and the cross-piece 24. The spring 16 is configured to urge the shield 18 distally away from the hub 12.

The clip 20 is disposed between the hub 12 and the shield 18. The clip 20 is arcuate, and, preferably, the clip 20 is a continuous or discontinuous annular ring having an inner opening 30 sized to permit passage therethrough of the shield 18.

The clip 20 is disposed so as to be fixed relative to the hub 12 or the shield 18. Preferably, and with reference to FIGS. 2 and 6, the shield 18 includes a groove 32 in which the clip 20 may be seated. Preferably, the shield 18 is disposed to telescope interiorly of the hub 12 with the clip 20 being located on an exterior face of the shield 18. With this arrangement, the inner opening 30 is preferably slightly larger than the groove 32 so that the clip 20 may move or rotate about the shield 18. In this manner, the clip 20 is rotatable about the shield 18 but not axially movable along the length of the shield 18. The clip 20 is preferably made of plastic. As will be appreciated by those skilled in the art, the shield 18 may be configured to telescope exteriorly of the hub 12, as shown in FIGS. 13-16. With this arrangement, the groove 32 is located on an interior face of the shield 18 with the clip 20 being seated therein.

Figure 2:
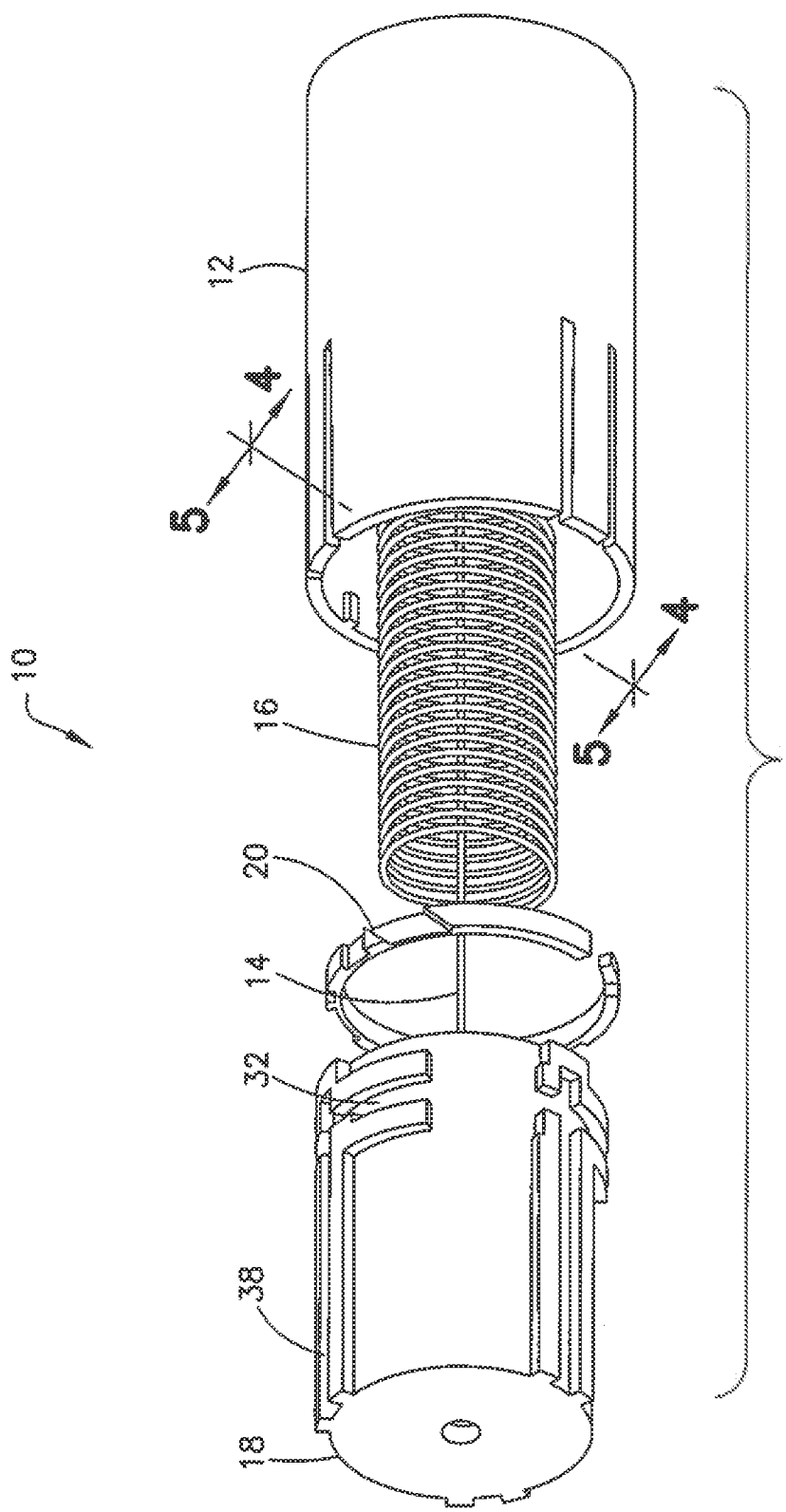

In the preferred arrangement of FIG. 2, the clip 20 is seated in the groove 32 and movable relative to the hub 12 with the shield 18. Alternatively, and with reference to FIGS. 17-27, a hub groove 34 may be formed in the hub 12. With this arrangement, the clip 20 may be seated in the hub groove 34 and move or rotate relative to the hub 12 but not move axially relative to the hub 12. The shield 18 is movable with this arrangement relative to the hub 12 and the clip 20.

The tab 22 is located depending on where the clip 20 is seated. In the preferred arrangement with the clip 20 seated in the groove 32 on the shield 18, the tab 22 is preferably formed on the hub 12. In the alternative, with the clip 20 seated in the hub groove 34 of the hub 12, the tab 22 is preferably formed on the shield 18. A notch 36 is formed on the clip 20 configured to allow passage of the tab 22 therethrough.

Figure 3:
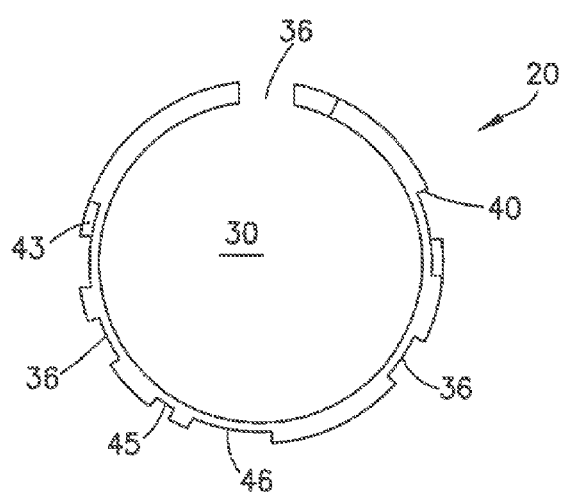
Figure 4:
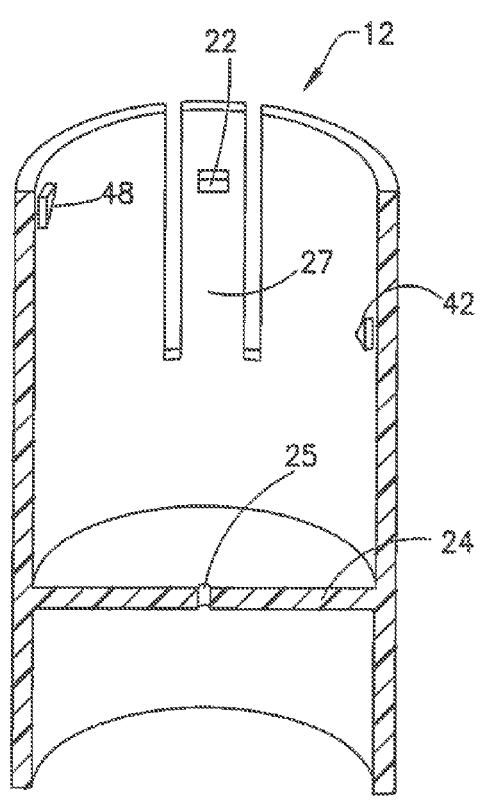
Figure 5:
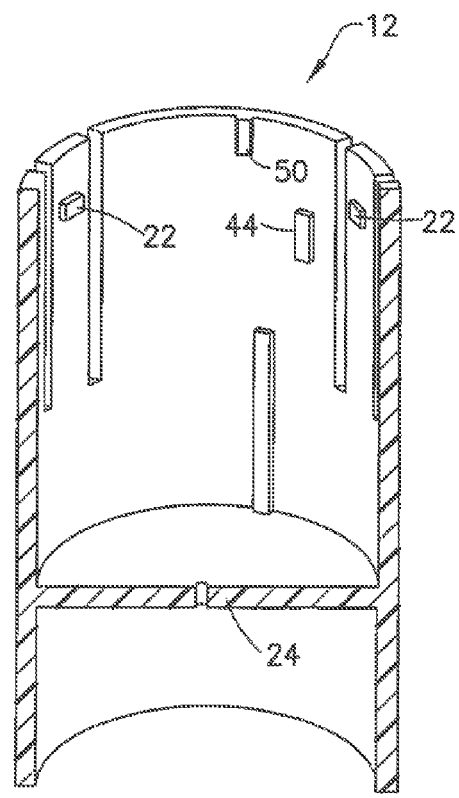

It is noted that one or more of the tabs 22 may be utilized with a corresponding number of the notches 36 being provided. By way of non-limiting example, and with reference to FIGS. 4 and 5, three of the tabs 22 may be provided. Correspondingly, three of the notches 36 may be provided on the clip 20 (FIG. 3). The notches 36 may be formed through the clip 20 so as to form a break in the clip 20 and/or the notches 36 may be formed of limited depth, as shown in FIG. 3. It is preferred that one of the notches 36 be formed through the clip 20 thus providing the clip 20 with deformable resilience that facilitates mounting the clip 20 about the shield 18. With reference to FIGS. 13-16, one of the tabs 22 may be utilized. For illustrative purposes, any reference herein to a singular of the tabs 22 or the notches 36 is not limiting and is intended to cover arrangements of one or more of the components.

Figure 17:
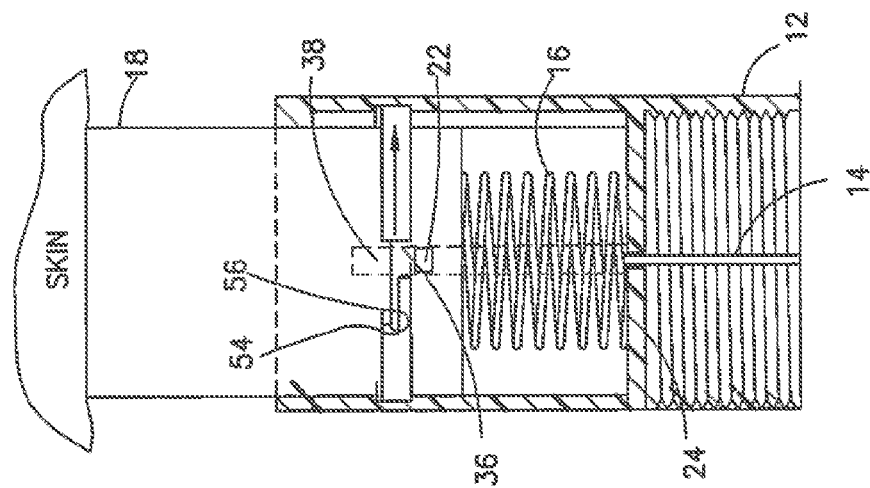

The clip 20 and the tab 22 coact together to releasably retain the shield 18 in a first locked state against the biasing force of the spring 16 thereby limiting distal movement of the shield 18 relative to the hub 12. Specifically, in the first locked state, the notch 36 is spaced from the tab 22 so as to not be in alignment therewith (FIGS. 6 and 17). The clip 20 and the tab 22 are relatively displaceable such that the notch 36 may be aligned with the tab 22. With the notch 36 being aligned with the tab 22, the shield 18 is released from the first locked state with the shield 18 being able to move distally, relative to the hub 12, under force of the spring 16 to a second shielded state where the distal end 28 of the needle 14 is covered by the shield 18. The specifics of this process may be altered depending on how the clip 20 is retained in the assembly 10.

With reference to FIGS. 6-12, operation of the assembly 10 is shown with the clip 20 being seated in the shield groove 32. With this arrangement, the clip 20 moves axially relative to the hub 12.

With reference to FIG. 6, the tab 22 is formed on the hub 12. A channel 38 is formed in the shield 18 in which the tab 22 extends. FIG. 6 depicts the first locked state with the notch 36 being spaced from the tab 22. With the tab 22 being located distally of the clip 20, the interengagement of the tab 22 and the clip 20 limits distal movement of the shield 18 under force of the spring 16. The shield 18, however, is free to move proximally. In this manner, the needle 14, particularly the distal end 28, may be sufficiently exposed to conduct an injection. Depending on the spacing and arrangement of the various elements of the assembly 10, the shield 18 may be positioned to initially cover, i.e., cover in the first locked state, any degree of the needle 14, including covering the entire needle 14. It may be desired, as shown in FIG. 6, to have a small extent of the needle 14 from the distal end 28 to be initially exposed in the first locked state so that priming of the needle 14 may be visually inspected.

To facilitate assembly of the assembly 10, the tab 22 may be located on a cantilevered arm 27 formed in the hub 12. The resilience of the cantilevered arm 27 allows for radially outwardly deflection of the tab 22, along with the cantilevered arm, in inserting the clip 20 past the tab 22 to the position shown in FIG. 6.

Figure 7:
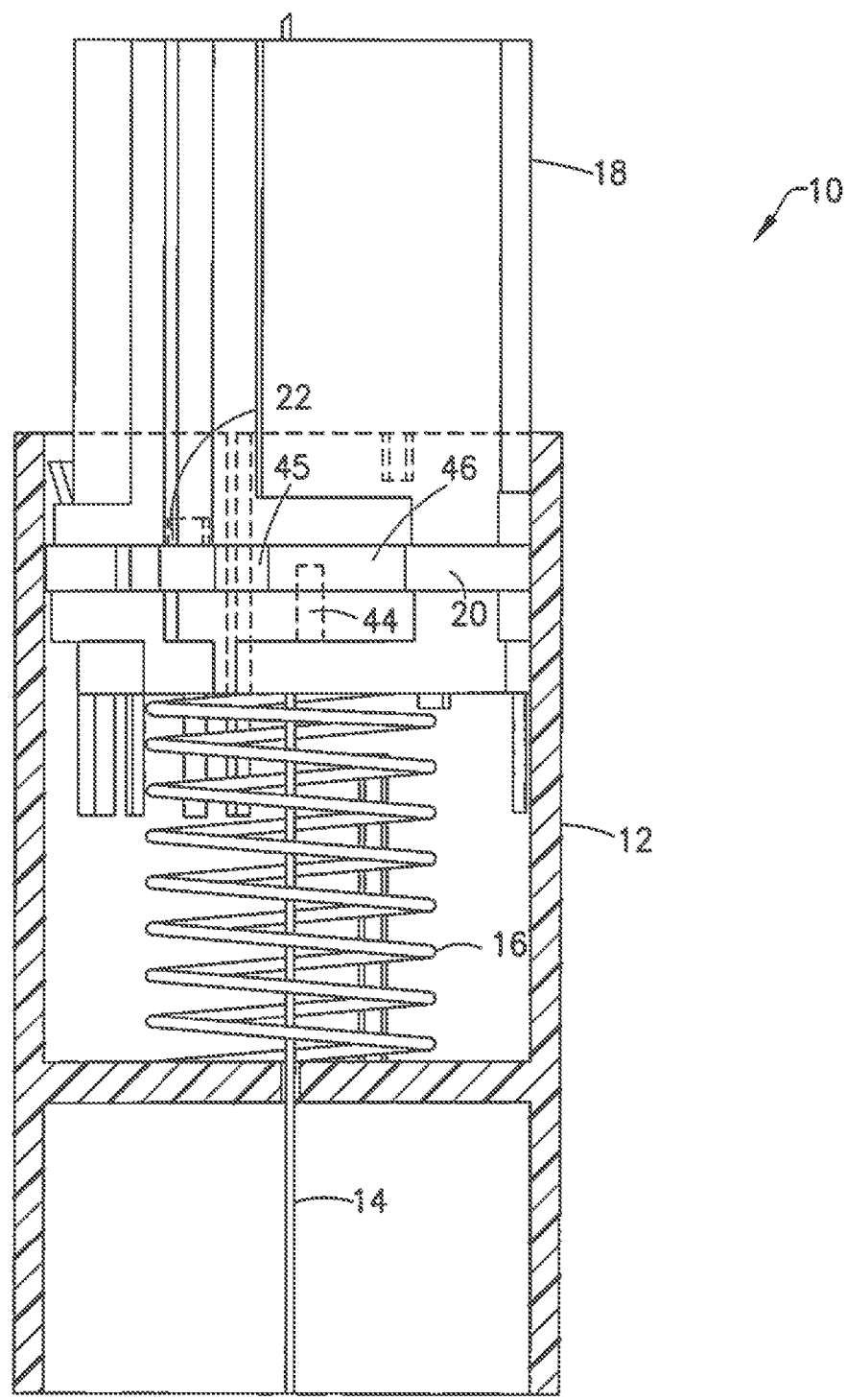
Figure 8:
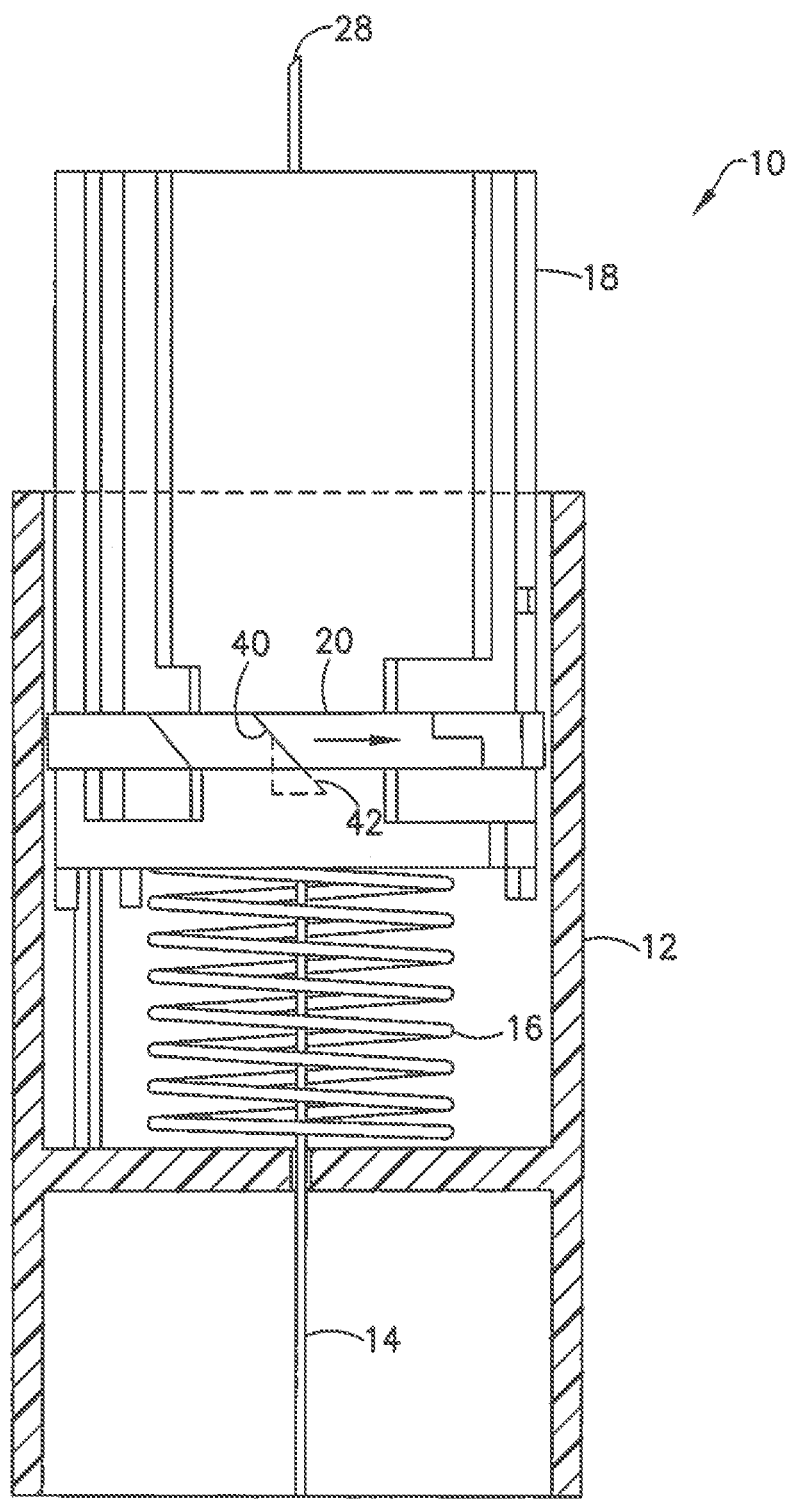
Figure 9:
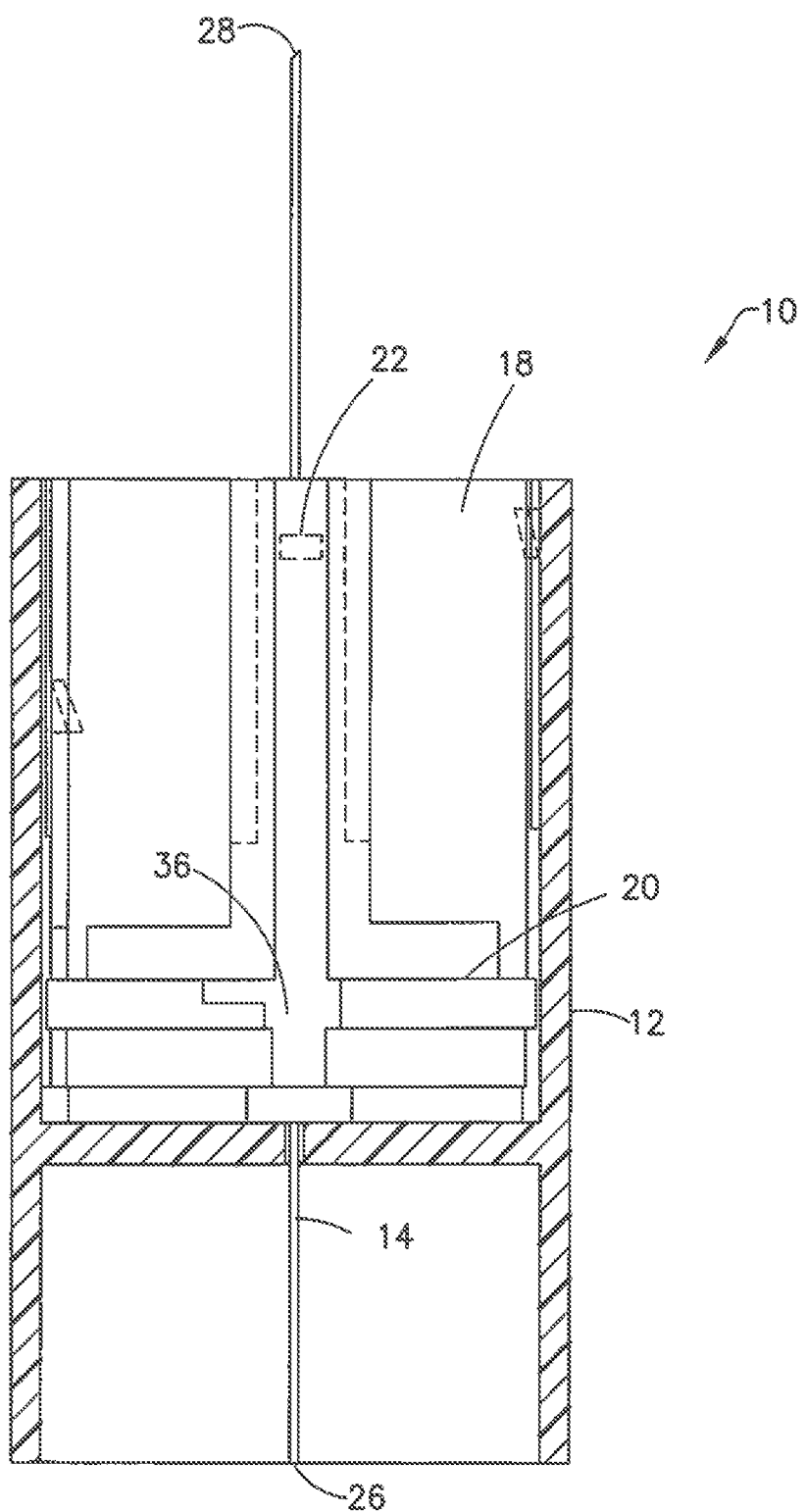

Movement of the clip 20, particularly rotation, is required to align the notch 36 with the tab 22 so as to release the shield 18 from the first locked state. As will be appreciated by those skilled in the art, any known arrangement for achieving rotation of the clip 20 consistent with the subject invention may be utilized. By way of non-limiting example, and with reference to FIGS. 3 and 4, complementary ramped surfaces 40, 42 may be provided on the hub 12 and the clip 20, respectively, which cooperatively cause the clip 20 to rotate upon sufficient proximal movement of the shield 18 relative to the hub 12. Preferably, in the first locked state, a protrusion 44 formed on the hub 12 extends into a recess 46 formed on the clip 20 (FIG. 7). The interengagement of the protrusion 44 and the recess 46 limits rotational movement of the clip 20 relative to the shield 18, particularly in the rotational direction necessary to align the notch 36 with the tab 22. With sufficient proximal movement of the shield 18, as shown in FIG. 8, the ramped surfaces 40, 42 are brought together. In addition, the recess 46 is moved clear of the protrusion 44. With sufficient proximal movement, the ramped surfaces 40, 42 cause movement of the clip 20, e.g., in the form of rotation as represented by the arrow in FIG. 8. As shown in FIG. 9, with sufficient rotation, the notch 36 is caused to align with the tab 22 so that the notch 36 may pass distally thereover under force of the spring 16 causing distal movement of the shield 18.

Alignment of the tab 22 and the notch 36 permits the shield 18 to be released from the first locked state. With rotation of the clip 22, the recess 46 is out of alignment with the protrusion 44. To permit distal movement of the shield 18 and avoidance of interengagement of the protrusion 44 with the clip 20, a by-pass channel 45 (FIG. 3) may be formed on the clip 20 sized and positioned to pass over the protrusion 44 during distal movement of the shield 18.

Figure 10:
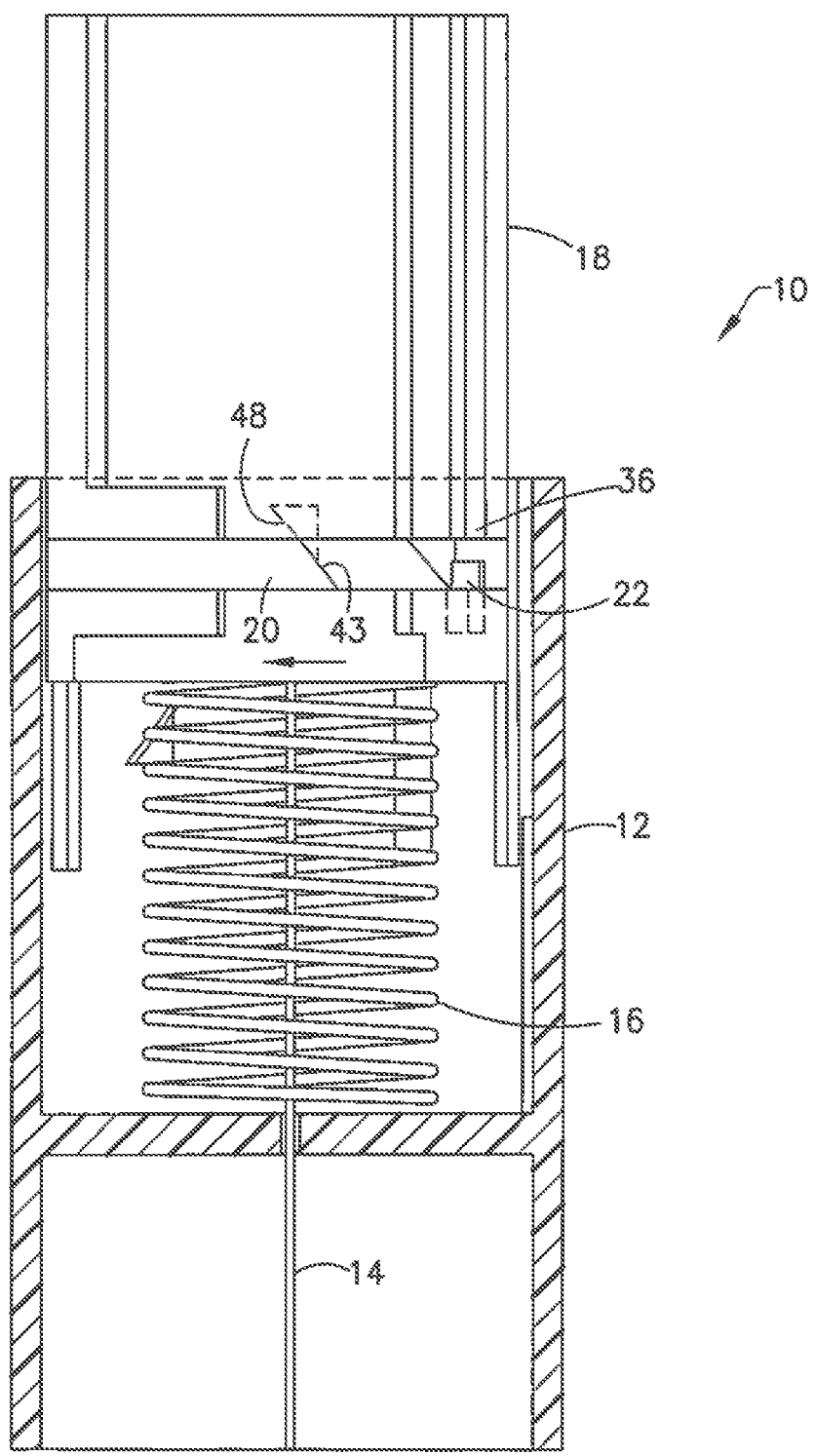
Figure 11:
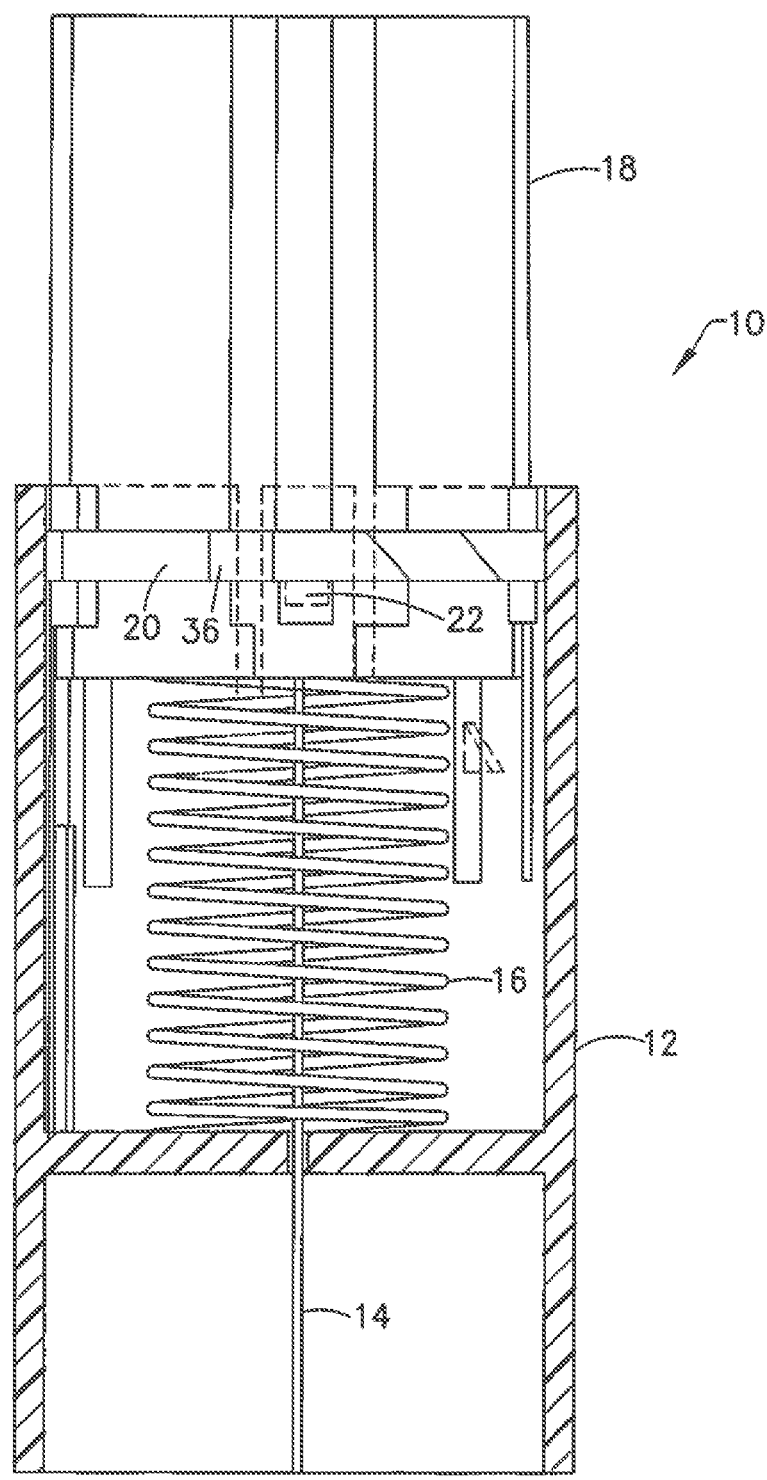
Figure 12:
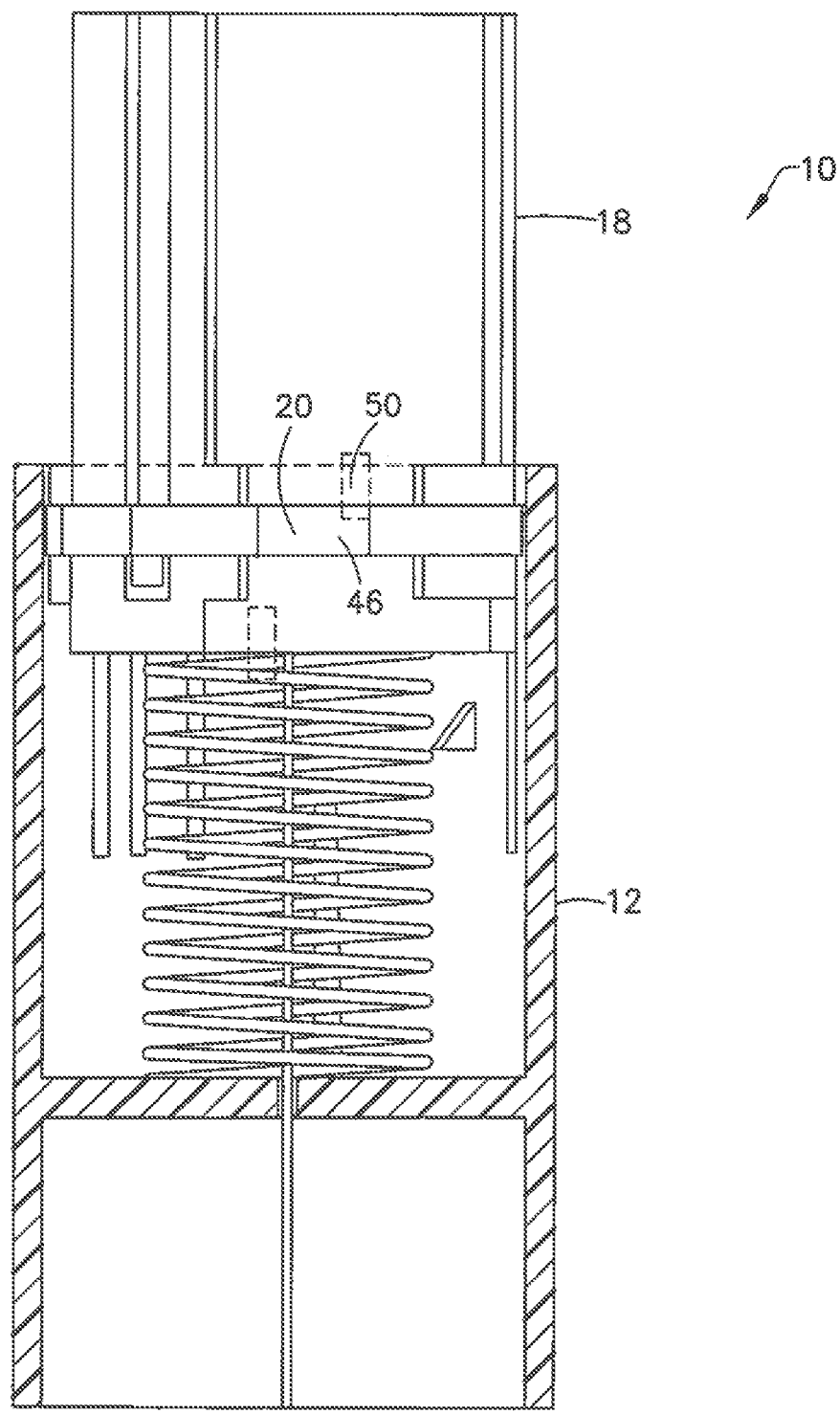

With sufficient distal movement of the shield 18, a secondary ramped surface 43, formed on the clip 20, comes into engagement with a complementary second ramped surface 48 formed on the hub 12 (FIG. 10). The secondary ramped surfaces 43 and 48 are configured to cause reverse rotation of the clip 20 back towards its initial state as found in the first locked state. With this rotation, the notch 36 comes out of alignment with the tab 22. As such, the tab 22 is located proximally of the clip 20 and spaced from the notch 36, as shown in FIG. 11. In addition, a secondary protrusion 50, formed on the hub 12, is urged into the recess 46 so as to prevent subsequent movement of the clip 20 thereafter (FIG. 12).

With reference to FIG. 9, the channel 38 is shown as travelling past the tab 22. The channel 38 includes a proximal end 52 (best shown in FIG. 6). With sufficient distal movement of the shield 18, the tab 22 is urged to the proximal end 52. The interengagement of the tab 22 and the proximal-end 52 limits further distal movement of the shield 18 under force of the spring 16. In addition, with the clip 20 being rotated back, as shown in FIG. 11, the tab 22 is located proximally of the clip 20. Proximal movement of the shield 18 is limited due to the interengagement of the tab 22 with the clip 20. With limited distal and proximal movement, the shield 18 may be locked in the second shielded state, particularly with the shield 18 covering the distal end 28 of the needle 14.

Figure 13:
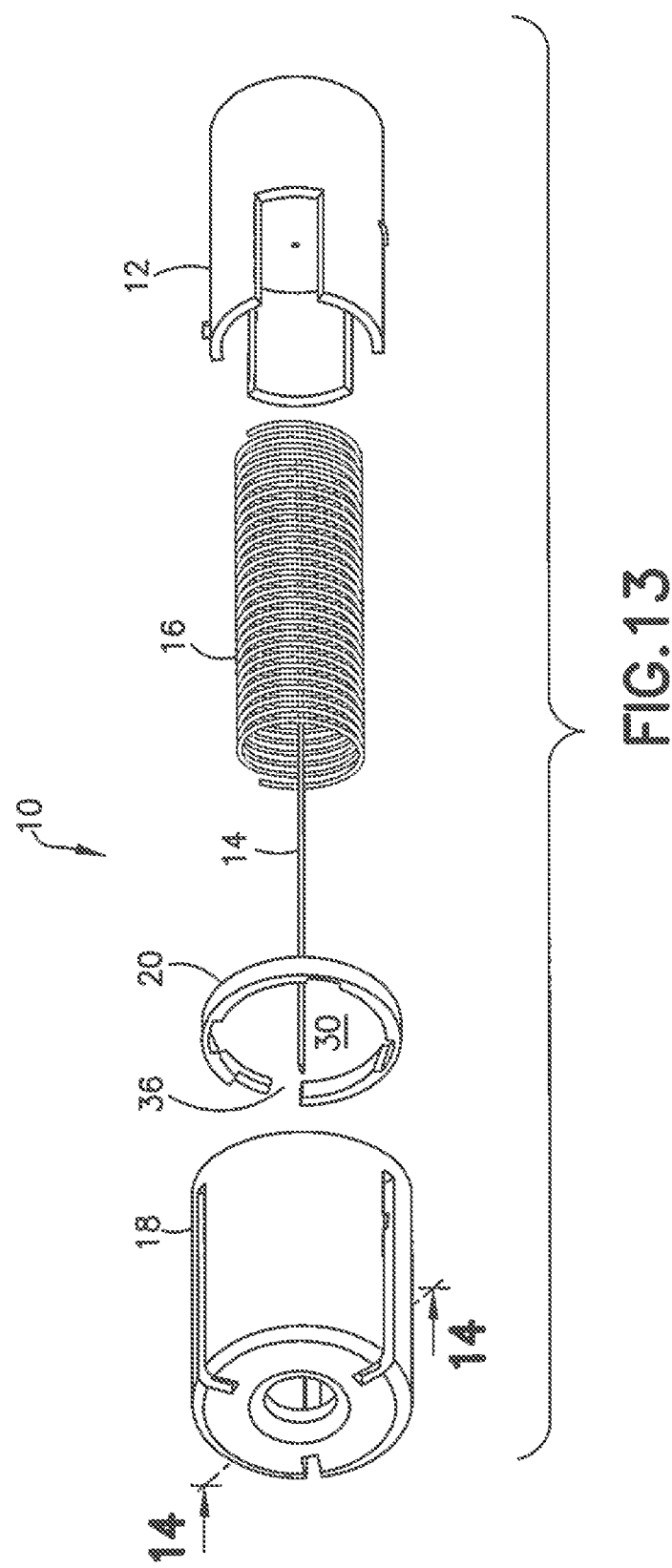

With reference to FIGS. 13-16, the device 10 is shown with the shield 18 being configured to telescope exteriorly of the hub 12. As shown in FIG. 14, the groove 32 is formed interiorly of the shield 18 and, as shown in FIGS. 15 and 16, the tab 22 and the ramped surfaces 42, 48 are located exteriorly of the hub 12. Also, as shown in FIG. 13, features on the clip 20 are located interiorly along the inner opening 30.

With reference to FIGS. 17-27, the device 10 is shown where the clip 20 is mounted into the hub groove 34. With this arrangement, the shield 18 may be configured to telescope over the hub 12 with the tab 22 and other elements formed on the hub 12 (e.g., the ramped surfaces 42, 48) being located on an external face thereof, or the shield 18 may be configured to telescope within the hub 12 as shown in FIGS. 17-26, with the tab 22 and other elements being located on an internal face of the hub 12. In addition, the hub groove 34 may be located interiorly of the shield 18 or exteriorly of the shield 18 (FIGS. 17-27). The clip 20 is correspondingly located with the features thereof being configured to cooperatively interact as described below.

With reference to FIGS. 17-26, operation of the assembly 10 is shown with the clip 20 being seated in the hub groove 34. With this arrangement, the clip 20 does not move axially relative to the hub 12.

With reference to FIG. 17, the tab 22 is formed on the shield 18, and the channel 38 is formed in the hub 12 in which the tab 22 extends. FIG. 17 depicts the first locked state with the notch 36 being spaced from the tab 22. With the tab 22 being located proximally of the clip 20, the interengagement of the tab 22 and the clip 20 limits distal movement of the shield 18 under force of the spring 16. The shield 18, however, is free to move proximally. In this manner, the needle 14, particularly the distal end 28, may be sufficiently exposed to conduct an injection. Depending on the spacing and arrangement of the various elements of the assembly 10, the shield 18 may be positioned to initially cover, i.e., cover in the first locked state, any degree of the needle 14, including covering the entire needle 14. It may be desired, as shown in FIG. 17, to have a small extent of the needle 14 from the distal end 28 to be initially exposed in the first locked state so that priming of the needle 14 may be visually inspected.

Figure 23:
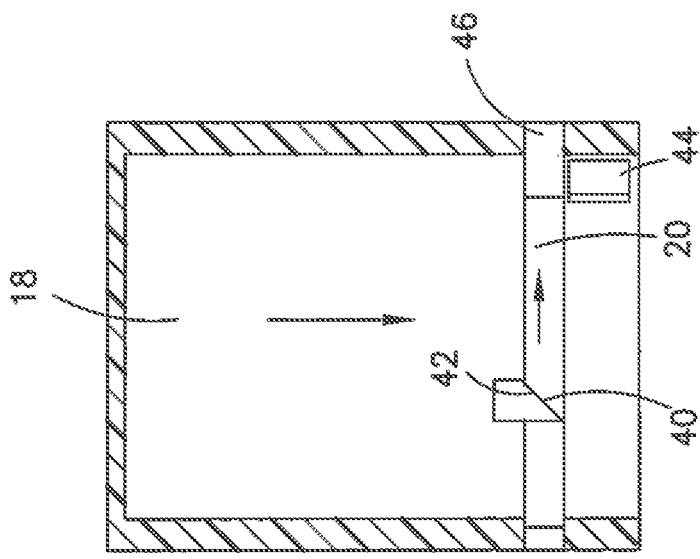
Figure 22:
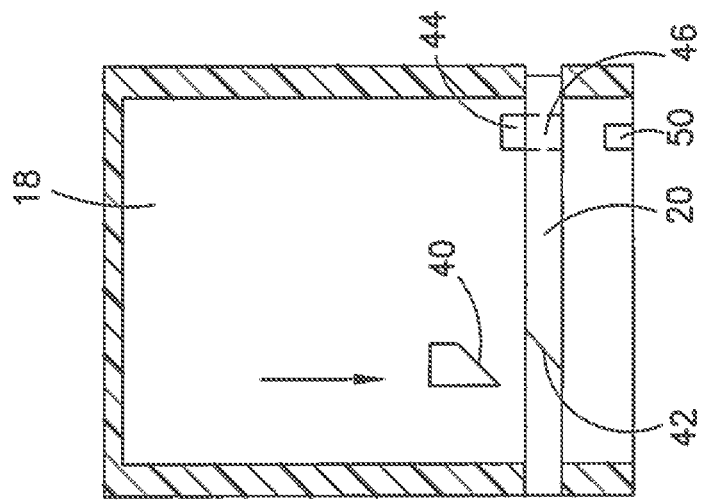
Figure 21:
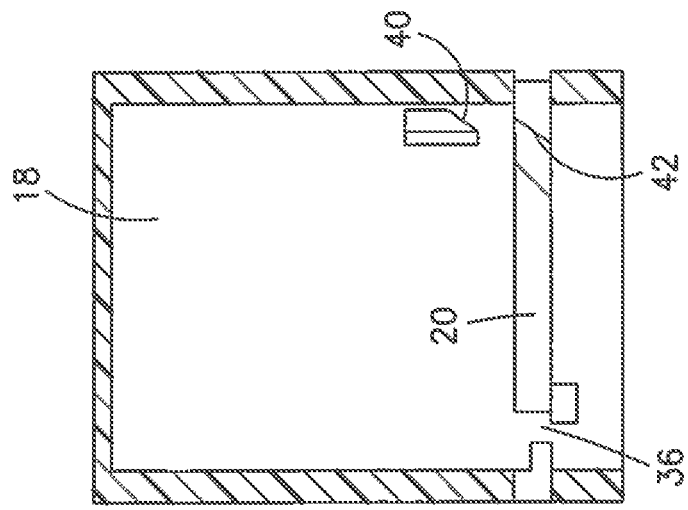

Movement of the clip 20, particularly rotation, is required to align the notch 36 with the tab 22 so as to release the shield 18 from the first locked state. As will be appreciated by those skilled in the art, any known arrangement for achieving rotation of the clip 20 consistent with the subject invention may be utilized. By way of non-limiting example, and with reference to FIGS. 21-26, the complementary ramped surfaces 40, 42 may be provided on the shield 18 and the clip 20, respectively, which cooperatively cause the clip 20 to rotate upon sufficient proximal movement of the shield 18 relative to the hub 12. Preferably, in the first locked state, the protrusion 44, formed on the shield 18, extends into the recess 46 formed on the clip 20. The interengagement of the protrusion 44 and the recess 46 limits the movement of the clip 20 relative to the shield 18. With proximal movement of the shield 18, as shown in FIGS. 22 and 23, the ramped surfaces 40, 42 are brought together, and the protrusion 44 is moved clear of the recess 46. With sufficient proximal movement, the ramped surfaces 40, 42 cause movement of the clip 20, e.g., in the form of rotation. As shown in FIG. 24, with sufficient rotation, the notch 36 is caused to align with the tab 22 so that the tab 22 may pass distally therethrough under force of the spring 16. Alignment of the tab 22 and the notch 36 permits the shield 18 to be released from the first locked state.

With sufficient proximal movement of the shield 18, the secondary ramped surface 43, formed on the clip 20, comes into engagement with the complementary second ramped surface 48 formed on the shield 18. The secondary ramped surfaces 43 and 48 are configured to cause reverse rotation of the clip 20 back towards its initial state as found in the first locked state. With this rotation, the notch 36 comes out of alignment with the tab 22. As such, the tab 22 is located distally of the clip 20 and spaced from the notch 36. In addition, the secondary protrusion 50, formed on the shield 18, is urged into the recess 44 so as to prevent subsequent movement of the clip 20 thereafter.

Figure 18:
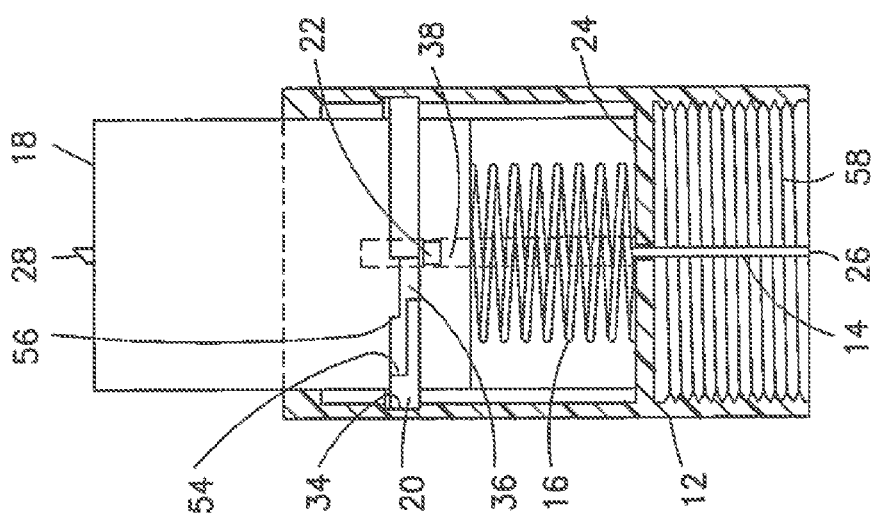
Figure 19:
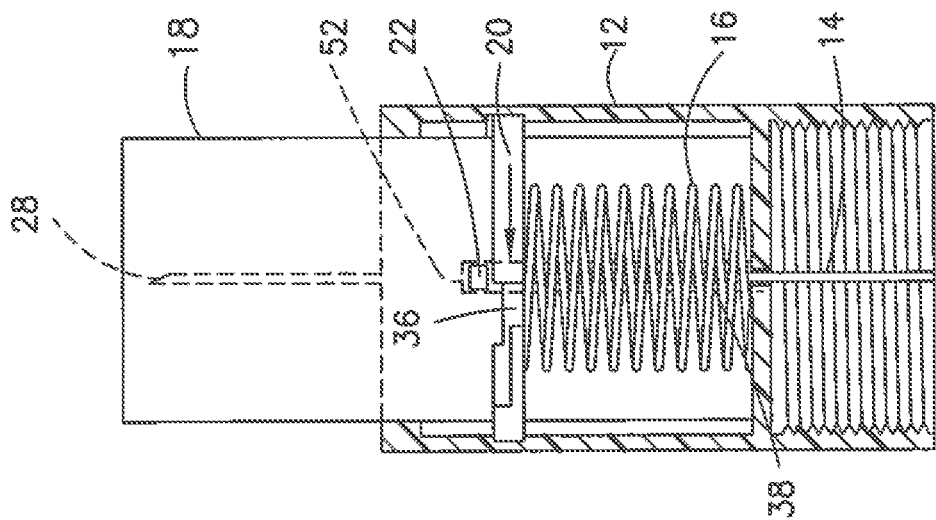
Figure 20:
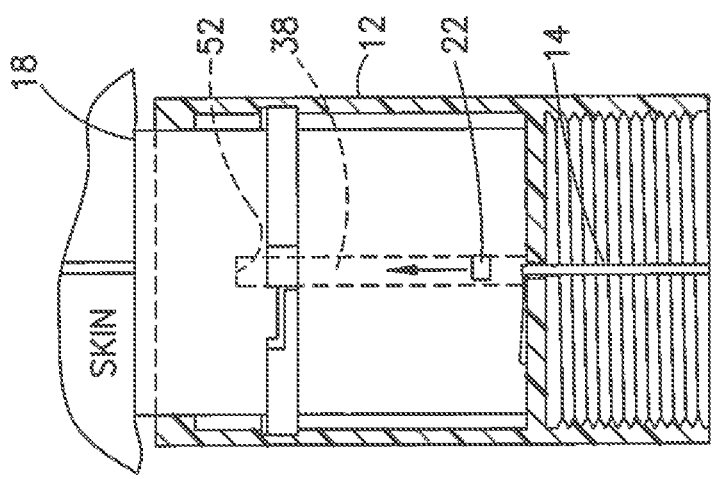

With reference to FIGS. 18-20, the tab 22 is shown as travelling along the length of the channel 38. After sufficient proximal movement of the shield 18, as shown in FIG. 18, the tab 22 and the notch 36 are caused to come into alignment and shield 18 is urged distally under force of the spring 16. The tab 22 is urged to the distal end 52 of the channel 38. The interengagement of the tab 22 and the distal end 52 limits further distal movement of the shield 18 under force of the spring 16. In addition, with the clip 20 being rotated back, as shown in FIG. 20, the tab 22 is located distally of the clip 20. Proximal movement of the shield 18 is limited due to the interengagement of the tab 22 with the clip 20. With limited distal and proximal movement, the shield 18 may be locked in the second shielded state, particularly with the shield 18 covering the distal end 28 of the needle 14.

The clip 20 and the hub 12 and/or the shield 18 may be formed with cooperating features which limit the extent of movement of the clip 20. For example, with reference to FIGS. 17 and 18, the clip 20 may be formed with a raised shoulder 54 positioned and located to engage a step 56 located on the hub 12 and/or the shield 18. The interengagement of the raised shoulder 54 and the step 56 limits the extent of movement of the clip 20, e.g., limiting movement to obtain alignment of the notch 36 and the tab 22 (FIG. 18).

The hub 12 may be provided with features 58 (FIG. 17) for mounting onto an injector, such as the body of a pen injector. The features 58 are preferably located proximally of the cross-piece 24. The features 58 may include threads and/or surface configuration (e.g., a Luer taper) for mounting onto an injector body. Alternatively, the hub 12 may be formed unitarily with or as a component of an injector body with the assembly 10 being pre-mounted thereto. This arrangement may be used for a single dose injector where replacement of the assembly 10 is not of concern.

What is claimed is:

1. A safety needle assembly comprising: a hub; a needle fixed to said hub, said needle having a distal end, formed for insertion into a patient, and a proximal end; a shield; a tab; a spring disposed between said shield and said hub configured to bias said shield distally relative to said hub; and a clip disposed between said hub and said shield, said clip having a notch formed thereon shaped to permit passage therethrough of said tab, wherein said clip is axially fixed relative to one of said hub or said shield and is rotatable with respect to said one of said hub or shield that said clip is axially fixed relative to; wherein said clip and said tab are engaged to form a first locked state and releasably retain said shield in the first locked state against the biasing force of said spring wherein the interengagement of the clip and the tab limits distal movement of said shield relative to said hub; wherein in said first locked state: said shield is movable proximally relative to said hub; and said notch is spaced from said tab; wherein said clip and said tab are relatively displaceable to align said notch with said tab and release said shield from said first locked state, thereby allowing said shield to move distally, relative to said hub, to a second shielded state; and wherein, in said second shielded state, said distal end of said needle is covered by said shield.

2. A safety needle assembly as in claim 1, wherein a predetermined extent of proximal movement of said shield, relative to said hub, allows for relative displacement of said clip and said tab so as to release said shield from said first locked state, allowing said shield to move to said second shielded state.

3. A safety needle assembly as in claim 1, further comprising a mounting means for mounting said pen needle assembly onto an injector body.

4. A safety needle assembly as in claim 1, wherein said distal end of said needle extends distally from said shield in the first locked state.

5. A safety needle assembly as in claim 1, wherein in said second shielded state, said tab is located distally of said clip with said notch being spaced from said tab, the interengagement of said clip and said tab limiting proximal movement of said shield relative to said hub.

6. A safety needle assembly as in claim 5, wherein said hub includes a channel, said channel terminating at a distal end, said tab being slidably disposed in said channel, wherein, in said second shielded slate, said tab is located at said distal end of said channel, the interengagement of said distal end of said channel and said tab limiting distal movement of said shield relative to said hub.

7. A safety needle assembly as in claim 1, wherein in said second shielded state, said tab is located proximally of said clip with said notch being spaced from said tab, the interengagement of said clip and said tab limiting proximal movement of said shield relative to said hub.

8. A safety needle assembly as in claim 7, wherein said shield includes a channel, said channel terminating at a proximal end, said tab being slidably disposed in said channel, wherein, in said second shielded state, said tab is located at said distal end of said channel, the interengagement of said distal end of said channel and said tab limiting distal movement of said shield relative to said hub.

\* \* \* \* \*